Figure 1:
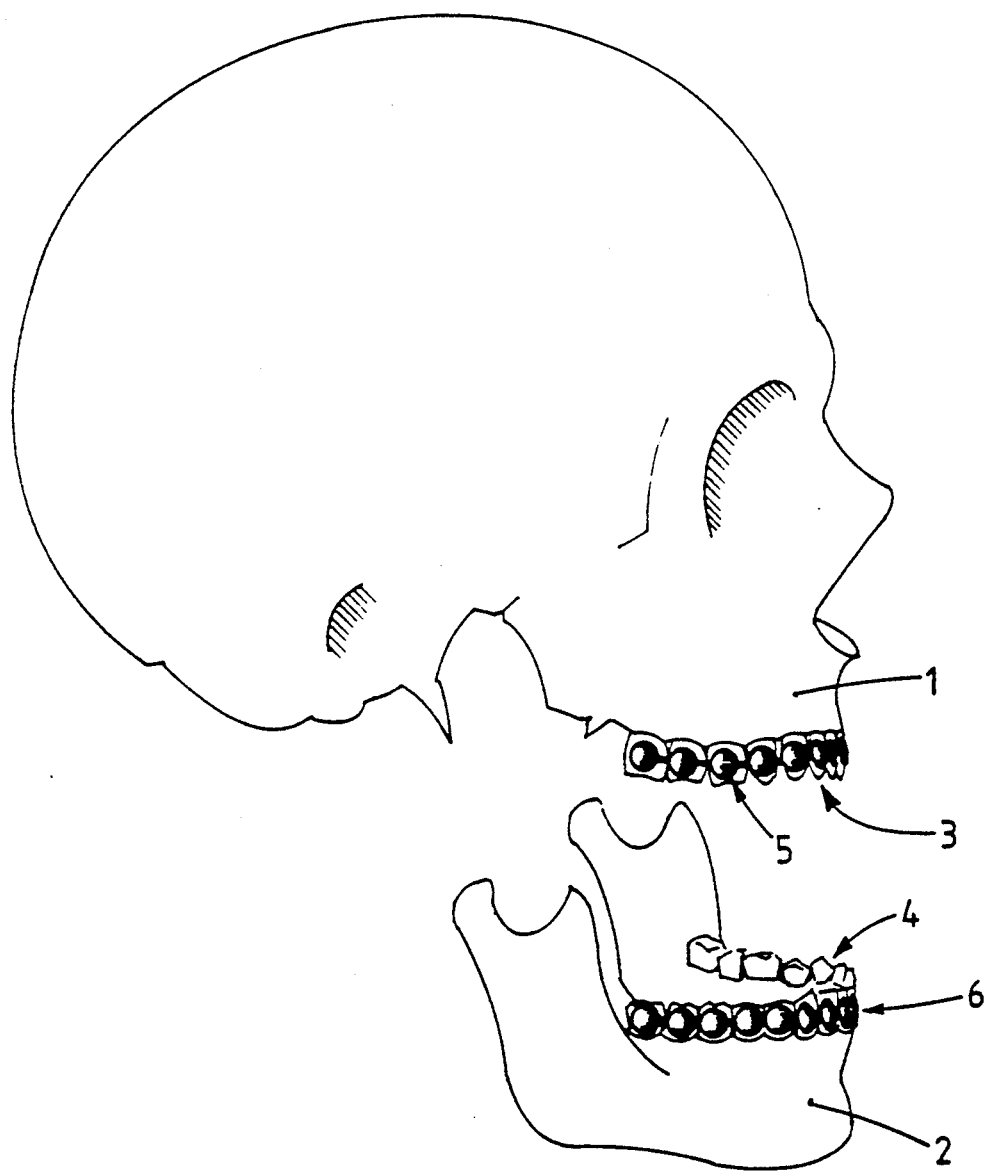

United States Patent [19]

Baer et al.

[11] Patent Number: 5,184,955
[45] Date of Patent: Feb. 9, 1993

[54] DEVICE FOR TEMPORARY DENTAL SPLINTING

[76] Inventors: Hans Baer, Bolleystrasse 12; Eduard Hirsbrunner, Clausiusstrasse 67, both of CH-8006 Zürich, Switzerland

[21] Appl. No.: 675,893
[22] PCT Filed: Aug. 28, 1990
[86] PCT No.: PCT/CH90/00202
§ 371 Date: Apr. 25, 1991
§ 102(e) Date: Apr. 25, 1991
[87] PCT Pub. No.: WO91/03212
PCT Pub. Date: Mar. 21, 1991

[30] Foreign Application Priority Data

Aug. 29, 1989 [CH] Switzerland ............. 03131/89

[51] Int. Cl.⁵ .................... A61C 5/00; A61C 3/00
[52] U.S. Cl. ............................. 433/215; 433/24
[58] Field of Search ............. 433/215, 9, 19, 24

[56] References Cited

U.S. PATENT DOCUMENTS

| | | | |
|---|---|---|---|
| 3,337,957 | 8/1967 | Reed | 433/215 |
| 3,505,736 | 4/1970 | Brader et al. | 32/14 |
| 3,903,601 | 9/1975 | Anderson et al. | 433/18 X |
| 4,107,844 | 8/1978 | Kurz | 32/14 A |
| 4,230,104 | 10/1980 | Richter | 433/19 X |
| 4,433,960 | 2/1984 | Garito et al. | 433/215 |
| 4,504,229 | 3/1985 | Garito et al. | 433/215 |
| 4,533,320 | 8/1985 | Pickarsky | 433/9 |
| 4,904,188 | 2/1990 | Baurmash | 433/215 |
| 4,915,630 | 4/1990 | Honig | 433/215 |
| 4,932,866 | 6/1990 | Guis | 433/24 |

OTHER PUBLICATIONS

International Search Report.

*Primary Examiner*—Robert P. Swiatek
*Assistant Examiner*—Nicholas D. Lucchesi
*Attorney, Agent, or Firm*—Wigman & Cohen

[57] ABSTRACT

For the temporary fixation of teeth, teeth rows or jaw parts, the device has a wire (9), on which annular composite carriers (7) are movably arranged. The composite carriers (7) can, for example, be flexible synthetic material rings of cross-section in the form of a truncated cone, through which the wire (9) is guided by means of two holes (8) arranged in the walls, which lie opposite one another, of the composite carriers (7).

The new splint makes possible the exact positioning of the composite carriers (7) which are arranged movably on the wire (9) and can be deformed at will by hand. After a caustic pretreatment of the tooth surface, the composite carriers (7), which are joined together by means of the wire (9), are placed on the teeth row to be connected and the cavities (A) of the composite carriers (7) are filled with composite (K) which surrounds on all sides the wire (9), which runs at a distance from the tooth surface, and connects both the wire (9) and the composite carriers (7) stably to the tooth surfaces.

Use for the temporary fixation of traumatically dislocated teeth after their repositioning or for post-operative immobilization of jaw parts. The decisive advantage of the device is that it can be used not only by dentists, but also in particular by non-dentally trained personnel, that is to say emergency doctors, surgeons and auxiliary medical personnel.

11 Claims, 4 Drawing Sheets

DEVICE FOR TEMPORARY DENTAL SPLINTING

The present invention relates to a device for the temporary fixation of teeth, teeth rows or jaw parts, especially in the case of tooth dislocation and in the case of surgical interventions on jaws.

Wounds in the area of the teeth and jaw lead in many cases to the loosening of teeth which can usually still be saved, providing that the necessary emergency treatment can take place quickly. Within the scope of such emergency treatment, the traumatized teeth are repositioned and must then subsequently be temporarily fixed to the undislocated neighboring teeth as quickly as possible by means of splinting. The immediate repositioning and splinting is an absolutely urgent prerequisite for successful treatment because of the rapid degeneration of the remaining periodontal tissue as well as the formation of blood clots in the alveolar area, which hinder the repositioning of the dislocated tooth. There is also the risk that after a certain period of time an initially partially dislocated tooth detaches itself and enters the windpipe.

Splints in the area of the teeth can also be necessary in order to bring about temporary, and more specifically intramandibular, intramaxillary or intermaxillary, fixations in jaw surgery.

According to a known currently used technique, the dislocated and repositioned tooth is connected to its neighboring teeth by means of a metal wire which, after an etching pretreatment, is fixed to the front surface of the teeth by means of composite material. The use of this known method requires special mastery of material and technique and can thus only be carried out by a dentist but not by the emergency doctor or the family doctor who in such cases is usually initially called in or available.

For the long-term after-treatment of gnathoorthopedic cases, it is known to stick rigid, metal holding elements, so-called brackets, onto the tooth surface. All these holding elements are connected to one another by means of a metal wire which is loosely guided through them. By means of tensioning and, if necessary, periodically retensioning of the wire, adjustive tensioning forces are transmitted via the holding elements, which in this case have the function of transmitting forces, to the teeth to be treated. This method also can only be applied by the dentist who is familiar with it; moreover, the rigidity of the holding elements renders their exact positioning more difficult.

It has also already been attempted to produce a dental splint with synthetic material only, that is to say without a wire-shaped connecting link. This method could not be implemented, however, at it is difficult to shape the synthetic material exactly and, on the other hand, it often does not withstand the forces which arise in the area of the teeth, the removal of the synthetic material has also proved difficult.

As the composite material must be removed again after a certain time, it is important that from the outset an amount which is as small as possible if this material is applied, in other words that the adhesion surface is delimited as exactly as possible, whereas on the other hand, however, the wire-shaped connecting link is nevertheless to be securely surrounded by composite at the respective fastening point and the formation of hollow points, in particular between wire and teeth surface, must be avoided.

It is the object of the present invention to propose a device for the temporary passive splinting of teeth, which can be applied without risk not only by dentists but also in particular by a family doctor, an emergency doctor, a jaw surgeon and if necessary by auxiliary medical personnel also.

The new device is on the one hand to limit the application of the composite, which secures the wire-shaped connecting link on the tooth surface, to the amount of composite actually necessary and on the other hand to make it possible exactly to select the position of the fastening point on the tooth surface.

The invention is directed to a wire-shaped connecting link and a plurality of composite carriers mounted thereon for receiving a composite material and limiting the area of each tooth surface to which the composite material is applied.

A number of exemplary embodiments of the device according to the invention are described below with reference to the attached drawing.

Figure 2:
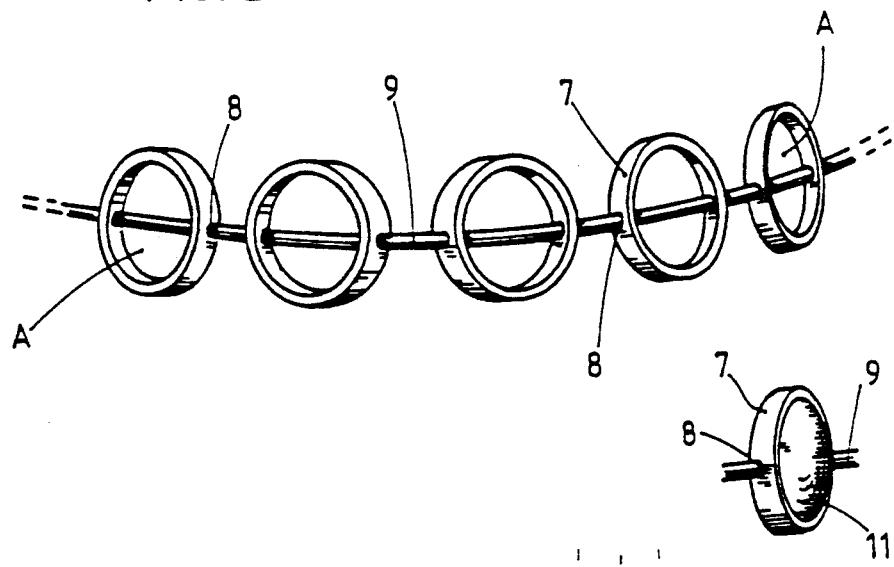
Figure 3:
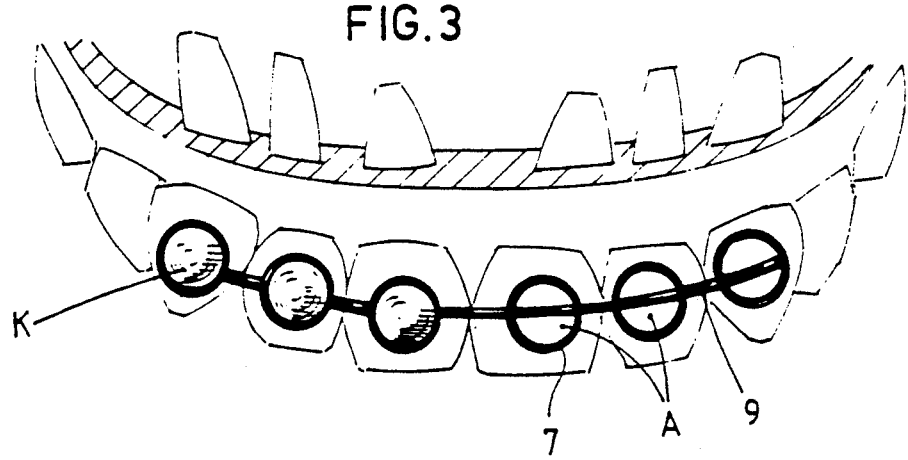
Figure 4:
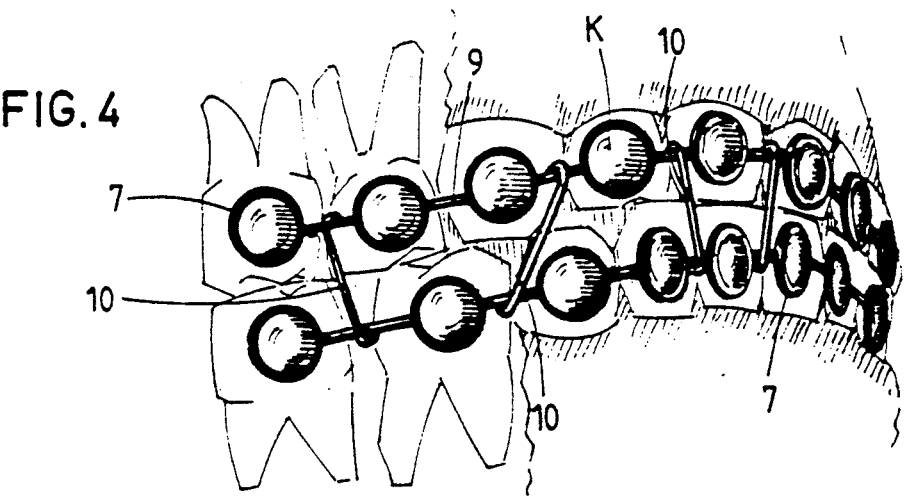
Figure 5:
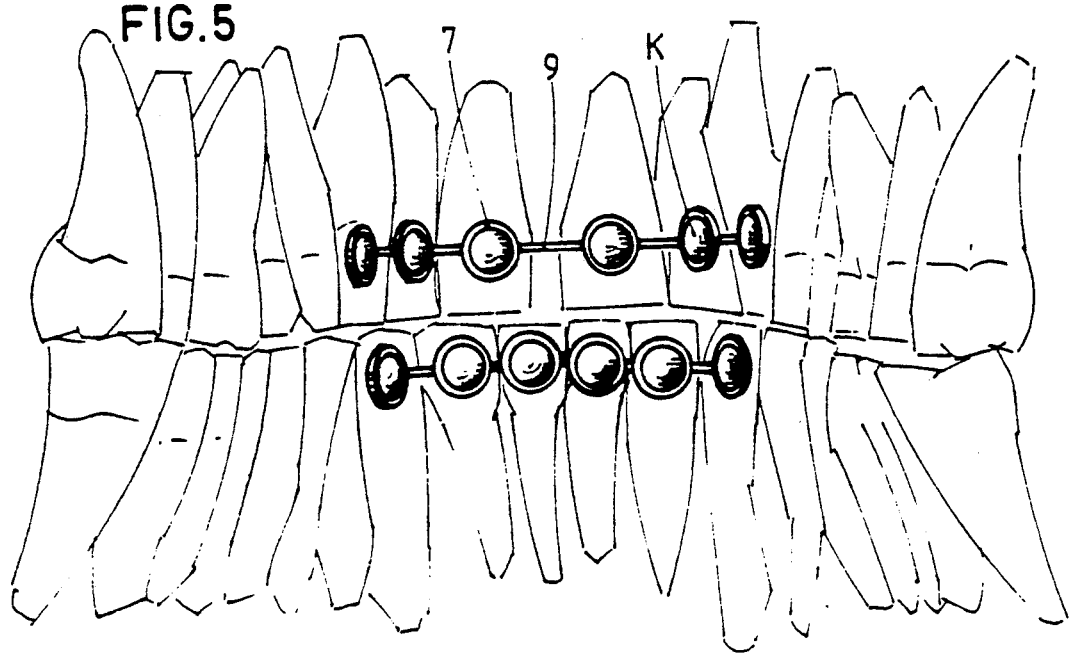

FIG. 1 illustrates the use of the device according to the invention on the external surfaces of the teeth on the maxillary and mandibular side, FIG. 2 shows a first embodiment of the device according to the invention, FIG. 3 shows the application of the device on the external surface of a teeth row on the maxillary side, FIG. 4 is a front view of an area of teeth, which has been splinted on the external surfaces of the teeth on both the maxillary and mandibular side, both jaw parts being connected in an intermaxillary manner, FIG. 5 shows a use on the internal surfaces of the teeth, lingually and palatally, FIGS. 6a-6e show a number of possible cross-sectional designs of annular composite carriers and FIGS. 7 to 11 illustrate examples of use on the oral and/or facial surfaces of the tooth parts on the maxillary and/or mandibular side.

FIG. 1 shows the teeth rows of upper jaw, maxilla, (1) and lower, mandibula, (2), on which an embodiment of the device according to the invention is shown by way of illustration. On the external surfaces of the teeth indicated by (3) and (4) respectively, splints (5) and (6) respectively are arranged, as they may be necessary, for example, in order temporarily to fix a traumatized tooth to its neighboring teeth or temporarily to immobilize an entire jaw part (in the case of a broken jaw, for example).

For the exact definition of the present invention, it is first of all to be pointed out that the same is intended neither for active splinting nor for the long-term orthopedic treatment of tooth misalignment or jaw anomalies. The field of use of the device according to the invention lies exclusively in the temporary passive fixation of teeth, teeth rows or jaw parts, such temporary passive fixation measures to be taken immediately after accidents or surgical interventions, which until now could not be carried out without calling an expert dentist or jaw surgeon. By virtue of the instruction according to the invention such temporary measures can now also be carried out easily by care personnel (family doctor, emergency doctor, surgeon, nursing personnel) present after an accident or an operation, by virtue of the simple application of the invention.

Accordingly, for the purposes of use of the device according to the invention, it is a prerequisite that any traumatically dislocated teeth have first been repositioned and according only a temporary fixation is still necessary.

To this end, a prefabricated splinting device is used as is illustrated in FIG. 2, for example. The device has a row of annular composite carriers (7), the wall parts of which lie opposite one another, in each case have a through hole (8), through which a wire (metal or synthetic material) (9) is drawn in such a manner that the composite carriers (7) can be moved along the wire.

The composite carriers (7) consist of a flexible synthetic material and are, for example, sections of an extruded synthetic material tube, so that they can be plastically deformed by means of finger pressure. Polymethylmethacrylate, for example, can be considered as the basic material for the composite carriers (7). The wire (9) can consist of either stainless steel (metal) or a suitable synthetic material.

This splinting device, which is illustrated schematically in FIG. 2, is then applied to the tooth part to be connected, after the intended fastening point has been pretreated with a caustic agent, in general 40% phosphoric acid. To this end, the splinting material, which can, for example, be kept in stock as goods sold by the meter, is cut to the required length and adapted approximately to the curvature of the relevant teeth row. After the composite carriers (7) have been placed on the intended fastening points, they can be optimally positioned by virtue of their movability on the wire (9) and of their elastic deformability. In this treatment stage, all the composite carriers (7) are consequently situated on the fastening points, while the wire (9) penetrates all the composite carriers (7) but does not touch the surfaces of the teeth, being guided rather at a distance in front of the same. The recesses (A), which are bounded by the composite carriers (7), are then filled with composite materials (K) and excess composite material is scraped off. In this manner, a fixation is simply achieved, which is agreeable to wear and which—provided the necessary accessories are available—can also be applied by the non-dentists in the shortest time.

In FIG. 3, the splint is shown again in detail and on a slightly larger scale using the example of a tooth fixation on the maxillary side. In this case, the left half of the splint has already been fastened with the three composite carriers (7) situated there to the adjoining tooth surfaces by means of composite material (K), whereas the recesses (A) of the remaining three composite carriers (7) are still to be provided with composite material.

In the event that the fixation method should prove to be inadequate in individual cases, it can of course be combined with known fixation means, for example an additional wire ligature which surrounds an individual tooth.

FIG. 4 shows a further use. Here, for example, the requirement may exist to fix maxilla and mandibula to one another temporary with regard to the healing of a jaw fracture, in order by these means to immobilize the point of fracture during the first period of the healing time. In this case, both the external surfaces of the upper (maxillary) and those of the lower (mandibular) teeth are provided with a splint. For the mutual, intermaxillary connection of the two jaws, the two wires (9) are coupled to one another by means of connection members (10). These connection members (10) can be, for example, metal, C-shaped, plastically deformable clips, self-fixing plastic loops or also simple wire ligatures.

A preferential design of composite carriers (7) is illustrated in connecting elements (10) characterized by direct attachment of the composite carriers. The preferential composite carriers (7) possess a hook-like appendage mechanism which relays a rounding off of the form thus providing the ergonomic design.

Practical use has demonstrated that this improved design of the composite carrier provides a very high level of wearing comfort for the patient.

One of the most important advantages of this particular design is the avoidance of accompanying tension producing untoward effects on and through the splint due to the direct attachment of connecting elements (10) to the composite carriers (7). Another important point to add is that connecting elements (10) produce undesirable torsion and shearing force when attached to wire component (9), which, even when performed by versed, proficient practitioners, are nevertheless very difficult to correct and supervise. The attachment of connective elements (10 and 14) directly to composite carriers (7) thereby enables utilization of splint also by less qualified personnel while still attaining good and stable results.

FIG. 5 shows schematically the application of the splint described to the internal tooth surfaces (lingual and palatal). This type of splinting has inter alia the advantage that it is obscured from view from the outside. In association with splints on the external tooth surface, an increase in the intramaxillary, intramandibular and also intermaxillary splinting stability can be achieved.

Figure 6:
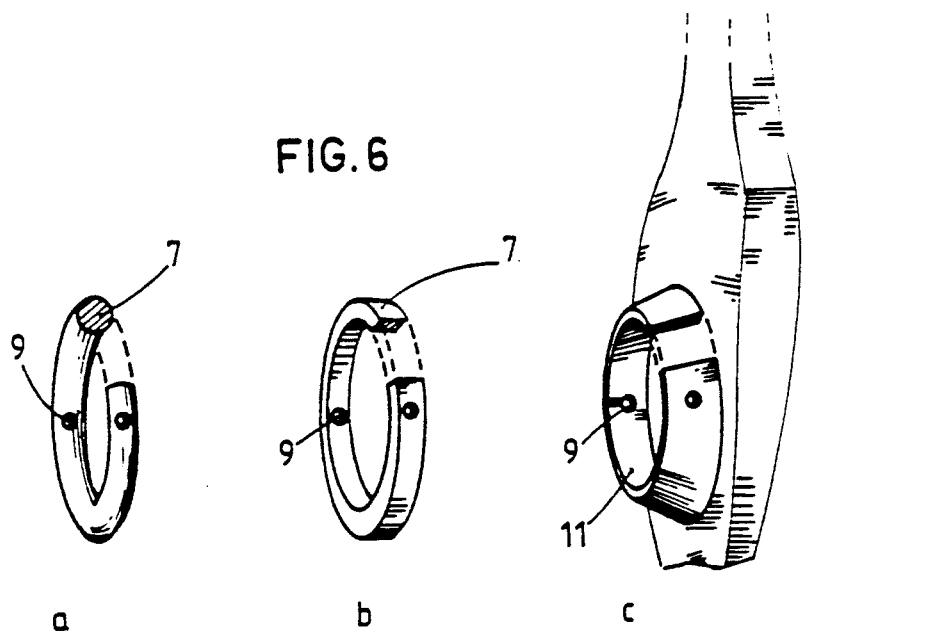
Figure 6:
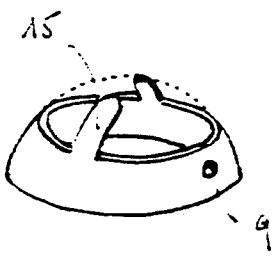
Figure 6:
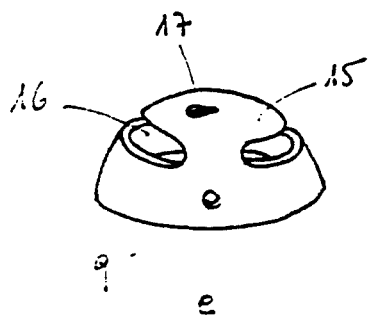

Within the scope of the present inventive idea, the decisive element is the composite carrier (7) which makes it possible to combine simple use of the device with good wearer-comfort and excellent stability. The three possible cross-sectional shapes of composite carriers (7), that is to say an annular ring (a) of circular cross-section, a cylindrical section (b), a truncated cone (c) and a dome-shaped alternative (d, e) are illustrated in FIG. 6, the adjoining tooth (Z) only being indicated in the case of the alternative in the form of a truncated cone (c). It can be seen here how the composite material (11) fills the cavity bounded by the composite carrier (7), in this connection surrounds on all sides the wire (9) situated at a distance from the tooth surface and securely connects both the composite carrier (7) and the wire (9) to the tooth surface. The composite carriers (7) can be round, oval or also polygonal according to requirements. The two through holes (8) (FIG. 2) for the wire (9) do not necessarily have to lie diametrically opposite one another, but can in special cases also be mutually offset.

Figure 7:
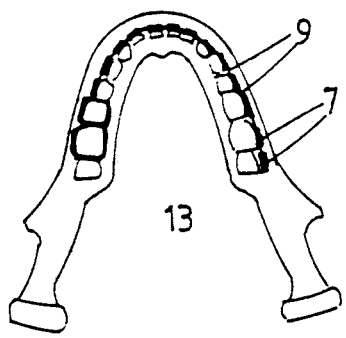
Figure 8:
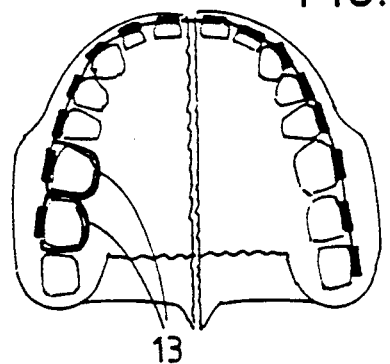
Figure 9A:
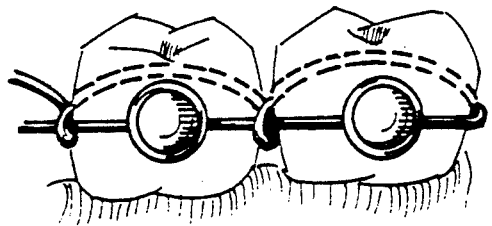
Figure 9:
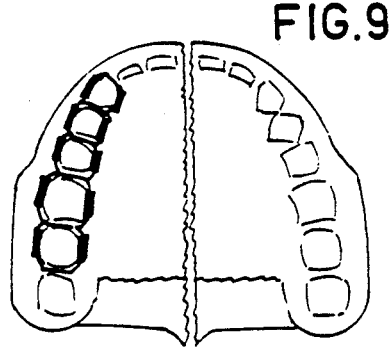
Figure 10:
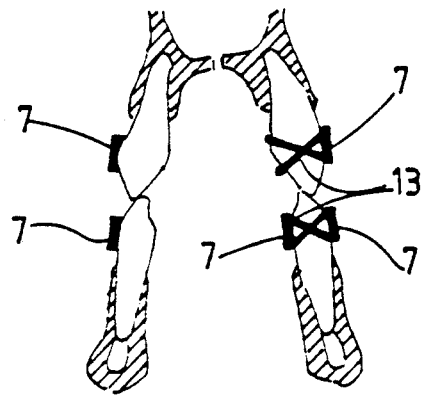
Figure 11:
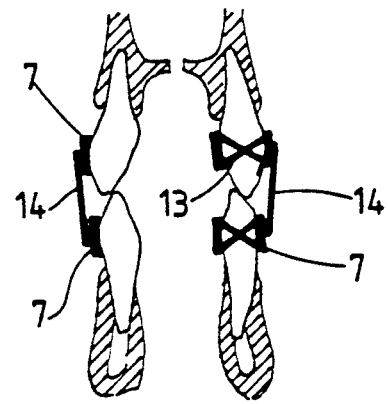

The main uses of the splint described are again schematically represented in FIGS. 7 to 11, in which FIG. 7 shows an intramandibular buccal splint with a wire ligature (13) applied to two teeth, FIG. 8 shows an intramaxillary buccal splint, likewise with additional, twofold securing by means of wire ligature (13), FIG. 9 shows a splint on both sides, that is to say buccal/lingual, in which the wires of the two splints are connected by means of wire ligatures (12), FIG. 10 shows an intramaxillary and intramandibular fixation which is secured by means of local wire ligatures (13) and FIG. 11 shows an intermaxillary fixation, in which the splint wires of the two jaws are secured to one another by means of plastically deformable metal clips, self-fixing synthetic material loops or wire ligatures (14).

The ergonomically designed composite carriers illustrated in FIGS. 6d and 6e are especially practical for use in antagonistic tooth fixation in both jaws. In the simplest case, the composite carriers (7) are annular with adaptation (15) in which the connective elements (10 and 14) allow hooking up. The preferred design of composite carrier (7) is illustrated in FIG. 6e.

The composite carrier (7) is characterized by enhancement through ergonomic principles as seen in the construction, a skull-capped manner with openings, (16 and 17) allowing a hooking up mechanism for connecting elements (10 and 14), as well as the possibility for complete filling with composite material. The openings possess dimensional characteristics specially designed to allow better application of working material, light-/energy source for curing the composite.

It is important to realize that further development of composite carrier lies in the hands of the specialist depending upon his or her knowledge and technical capability. Of utmost importance is that design of the composite carrier may also include multiple connecting elements (9), e.g. a convenient way for fixation between anterior and posterior splints. It must also be understood that the convenient use, based upon this innovative splinting device and the fricarive contact of the composite carriers with connector (9), whereby connector (9) requires use of a square wire, contributes to a reliable result.

We claim:

1. A device for the temporary fixation of teeth, teeth rows or jaw parts, as for example in the case of tooth dislocation or in the case of surgical interventions on jaws, comprising:
   a wire-shaped connecting link, said link adapted to be anchored on at least one of external and internal tooth surfaces of each of a number of neighboring teeth, and
   a row of annular composite carriers arranged movably on said connecting link, said composite carriers made from a flexible synthetic material, each said composite carrier bounding a recess which is adapted to receive and limit spreading of a composite material to be applied to each tooth surface, each said composite carrier having walls which lie opposite one another and adapted for said connecting link to pass therethrough,
   wherein said device is affixed to said teeth by application of a composite material to each tooth surface and wherein further, after application of said composite material, said connecting link lies at a distance from said tooth surfaces and is surrounded on all sides by said composite material.

2. The device as in claim 1, wherein the annular composite carriers have, on each of two sides which lie substantially opposite one another, a through hole, through which the wire-shaped connecting link is guided.

3. The device as in claims 1 or 2, wherein the composite carriers have an ergonomic design.

4. The device as in claim 3, wherein each composite carrier is a mechanism having an appendage in the form of a hook.

5. The device as in claim 3, further comprising openings in the composite carriers which are consipated for ease in filling and curing of composite material.

6. The device as in claim 3 wherein the wire-shaped connecting link is made of a material selected from the group consisting of stainless steel and an elastically deformable biocompatible material and the composite carriers are made of plastically deformable synthetic material.

7. The device as in claim 2 wherein the wire-shaped connecting link is made of a material selected from the group consisting of stainless steel and an elastically deformable biocompatible material and the composite carriers are made of a plastically deformable synthetic material.

8. The device as in claim 1, wherein the wire-shaped connecting link is made of a material selected from the group consisting of stainless steel and an elastically deformable biocompatible material and the composite carriers are made of a plastically deformable synthetic material.

9. A method for the temporary fixation of teeth, teeth rows or jaw parts, as for instance in the case of tooth dislocation or in the case of surgical interventions on jaws, comprising the steps of:
   providing a connecting device having a wire-shaped connecting link and a row of annular composite carriers arranged movably thereon, each said composite carrier bounding a recess which is adapted to receive and limit spreading of a composite material placed therein,
   positioning said connecting device over at least one of an external and an internal tooth surface at each of a number of neighboring teeth,
   affixing said connecting device by applying a composite material to each tooth surface in an area corresponding to each said composite carrier, such that said connecting link is surrounded by said composite material and lies at a distance from said tooth surfaces.

10. A method as in claim 9 for the mutual, intermaxillary fixation of maxilla and mandible, further comprising the steps of anchoring said wire-shaped connecting link on the maxillary side of a patient and coupling the mandibular side of a patient by providing connecting members.

11. A method as in claim 9 for antagonistic intermaxillary fixation of maxilla and mandible, further comprising connection of maxilla and mandible by tooth-based anchoring of said device, maxillary and mandibular.

* * * * *

UNITED STATES PATENT AND TRADEMARK OFFICE
CERTIFICATE OF CORRECTION

PATENT NO. : 5,184,955
DATED : February 9, 1993
INVENTOR(S) : Hans BAER et al It is certified that error appears in the above-identified patent and that said Letters Patent is hereby corrected as shown below:

Column 3, line 56, "temporary" should be --temporarily--.

Column 4, line 19, after "of" insert --the--.

Column 5, claim 1, line 35, "jaws." should be --jaws,--.

Signed and Sealed this

Eleventh Day of January, 1994

Attest:

BRUCE LEHMAN

Attesting Officer    Commissioner of Patents and Trademarks